US00PP09752P

United States Patent [19]

Kordes

[11] Patent Number: Plant 9,752

[45] Date of Patent: Dec. 17, 1996

[54] HYBRID TEA ROSE PLANT NAMED 'KORLIS'

[75] Inventor: Wilhelm Kordes, Sparrieshoop, Germany

[73] Assignee: Bear Creek Gardens, Inc., Medford, Oreg.

[21] Appl. No.: 596,003

[22] Filed: Feb. 2, 1996

[51] Int. Cl.[6] ..... A01H 5/00

[52] U.S. Cl. ..... Plt./18

[58] Field of Search ..... Plt./11, 17, 18, Plt./19

*Primary Examiner*—Howard J. Locker

*Attorney, Agent, or Firm*—Klarquist Sparkman Campbell Leigh & Whinston

[57] ABSTRACT

A new Hybrid Tea rose plant having long straight stems, large bud, large open flower, long vase life, stable flower color, and good production as a cut flower.

1 Drawing Sheet

The present invention relates to a new and distinct variety of rose plant of the hybrid tea class which was originated by me by crossing the variety Tanrikas, U.S. Plant Pat. No. 8,618, with an unnamed seedling.

The primary objective of this breeding was to produce a new rose variety having the good vase life and good yield of the female parent combined with the large bud and flower size and long stems of the orange red unnamed hybrid tea male seedling. The objective was substantially achieved, along with other desirable improvements, as evidenced by the following unique combination of characteristics that are outstanding in the new variety and that distinguish it from its parents, as well as from all other varieties of which I am aware:

1. Good production as a cut flower hybrid tea;
2. Large bud size;
3. Large open flower;
4. Long straight stems; and
5. Stable flower color.

Asexual reproduction of this new variety by budding, as performed at Wasco, Calif., and Sparrieshoop, Germany, shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—TANrikas.

*Pollen parent.*—Unnamed seedling.

Classification:

*Botanical.*—*Rosa hybrida.*

*Commercial.*—Hybrid tea.

FLOWER

Observations made from specimens grown in a greenhouse environment in Somis, Calif., and Sparrieshop, Germany, from January through December, 1995.

Blooming habit: Continuous.

Bud:

*Size.*—2 inches long when the petals start to unfurl.

*Form.*—The bud form is long, pointed ovoid.

*Color.*—When sepals first divide, bud color is Red Purple Group 62A. When half blown, the upper sides of the petals are Red Purple Group 62A, and the lower sides of the petals are Red Purple Group 62A.

*Sepals.*—Color: Green Group 139C. Surface texture: Covered in fine hairs. There are three normally to heavy appendaged sepals. There are two unappendaged sepals with hairy edges.

*Receptacle.*—Color: Green Group 143C. Shape: Funnel. Size: Slender (¼"×½"). Surface: Smooth.

*Peduncle.*—Length: Long (4"). Surface: Prickly, many small prickles. Color: Medium green. Strength: Stiff, erect.

Bloom:

*Size.*—Large. Average open size is 4½ to 5 inches.

*Borne.*—Singly.

Stems.—Long, strong. Average length is about 22 inches to 28 inches.

*Production.*—Good, averaging around 23 stems per plant per year.

*Form.*—When first open: High center. Permanence: Flattens, all petals curl, quill fashion.

*Petalage.*—Number of petals under normal conditions: 30.

*Color.*—The upper side of the petals is Red Purple Group 62A. The reverse side of the petals is Red Purple Group 62A. The base of each petal has a small color spot of Yellow Group 5B (¼"×¼"). The major color on the upper side is Red Purple Group 62A.

*Variegations.*—None.

*Discoloration.*—The general tonality at the end of the first day: No change. At the end of the third day: No change. On the plant the color will fade to Red Purple Group 68C by day 5. In the vase, there is no color change to day 10.

*Fragrance.*—Slight.

Petals:

*Texture.*—Thick.

*Shape.*—Round.

*Form.*—Tips slightly recurved, edges slightly quilled.

*Arrangement.*—Imbricated, with few petaloids in the center.

*Persistence.*—Drop off cleanly.

*Lastingness.*—On the plant: Long (6–7 days). As a cut flower: Long (10–12 days).

Reproductive parts:

*Anthers.*—Size: Medium. Quantity: Many. Color: Yellow. Arrangement: Regular around styles, mixed with occasional petaloids.

*Filaments.*—Color: Yellow.

*Pollen.*—Color: Lemon yellow.

*Styles.*—Color: Greenish white with pink on the lower half of the style.

*Stigmas.*—Color: Greenish white.

Form: Bush.

Growth: Vigorous, upright; branching. In the greenhouse under constant cutting, the plant will easily reach a height of 6 to 7 feet.

Foliage:

*Number of leaflets on normal mid-stem leaves.*—5 or occasionally 7.

*Size.*—Large (6"×5").

*Quantity.*—Abundant.

*Color.*—New foliage: Little anthocyanin present. Upper surface: Green 143A. Lower surface: Greyed Red 181B. Old foliage: Upper surface: Green Group 137A. Lower surface: Green Group 137D.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole underside.*—Smooth, with occasional prickles.

*Stipules.*—Medium (½"), serrated, bearded.

*Disease resistance.*—Resistant to mildew under normal growing conditions at Somis, Calif. As this is a greenhouse cut flower rose, it has not been tested for rust or blackspot.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium (¼"–⅜"), hooked downward.

*Color when young.*—Red.

Small prickles:

*Quantity.*—On main stalks: None. On laterals: None.

I claim:

1. A new and distinct variety of rose plant of the Hybrid Tea class, substantially as herein shown and described, characterized particularly as to novelty by the unique combination of long straight stems, large bud, large open flower, good vase life, stable flower color, and its good production as a cut flower Hybrid Tea rose.

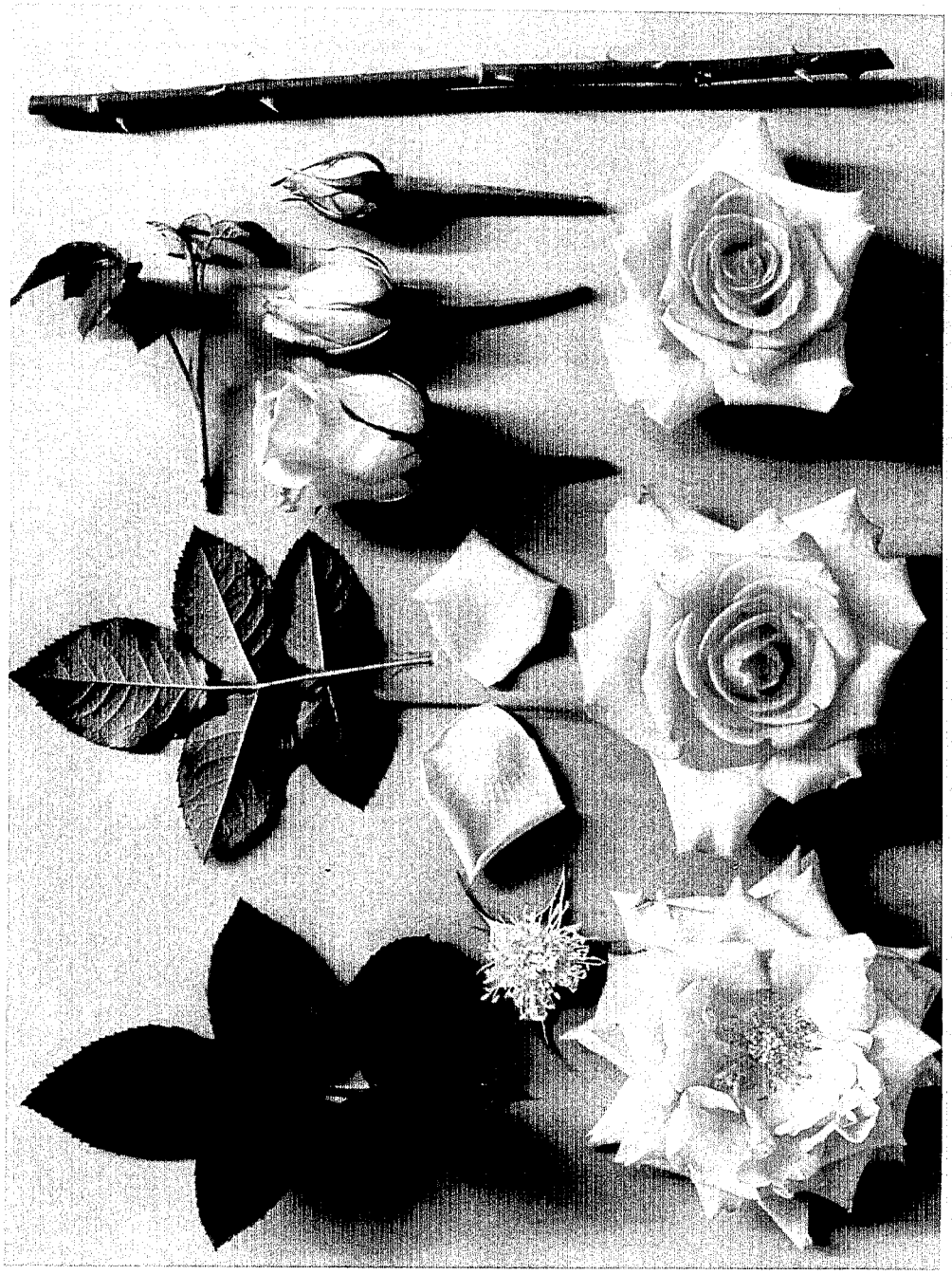

* * * * *